United States Patent
Thinon et al.

(10) Patent No.: US 12,071,509 B2
(45) Date of Patent: Aug. 27, 2024

(54) PROCESS FOR THE PRODUCTION OF A TEREPHTHALATE POLYESTER FROM A MONOMER MIXTURE COMPRISING A DIESTER

(71) Applicant: IFP Energies Nouvelles, Rueil-Malmaison (FR)

(72) Inventors: Olivier Thinon, Rueil-Malmaison (FR); Thierry Gauthier, Rueil-Malmaison (FR)

(73) Assignee: IFP ENERGIES NOUVELLES, Rueil-Malmaison (FR)

( * ) Notice: Subject to any disclaimer, the term of this patent is extended or adjusted under 35 U.S.C. 154(b) by 588 days.

(21) Appl. No.: 17/427,121

(22) PCT Filed: Jan. 27, 2020

(86) PCT No.: PCT/EP2020/051845
§ 371 (c)(1),
(2) Date: Jul. 30, 2021

(87) PCT Pub. No.: WO2020/156966
PCT Pub. Date: Aug. 6, 2020

(65) Prior Publication Data
US 2022/0135735 A1    May 5, 2022

(30) Foreign Application Priority Data
Feb. 1, 2019 (FR) ...................................... 1901023

(51) Int. Cl.
C08G 63/80       (2006.01)
C08G 63/183      (2006.01)
C08G 63/85       (2006.01)
C08J 11/24       (2006.01)

(52) U.S. Cl.
CPC ........... *C08G 63/183* (2013.01); *C08G 63/80* (2013.01); *C08G 63/85* (2013.01); *C08J 11/24* (2013.01); *C08J 2367/02* (2013.01)

(58) Field of Classification Search
USPC ........................................................ 528/229
See application file for complete search history.

(56) References Cited

U.S. PATENT DOCUMENTS

| | | | |
|---|---|---|---|
| 4,001,187 | A | 1/1977 | Itabashi et al. |
| 4,146,729 | A † | 3/1979 | Goodley |
| 4,334,090 | A | 6/1982 | Donaldson |
| 5,502,247 | A | 3/1996 | Bartos et al. |
| 5,504,121 | A | 4/1996 | West |
| 5,635,584 | A | 6/1997 | Ekart et al. |
| 5,869,543 | A | 2/1999 | Boos et al. |
| 6,815,525 | B2 | 11/2004 | DeBruin |
| 7,193,104 | B2 | 3/2007 | Inada et al. |
| 10,544,276 | B2 | 1/2020 | Charra et al. |
| 2006/0074136 | A1 | 4/2006 | Smith et al. |
| 2015/0105532 | A1 | 4/2015 | Allen et al. |
| 2019/0002632 | A1 † | 1/2019 | Hwang |

FOREIGN PATENT DOCUMENTS

| | | |
|---|---|---|
| EP | 0865464 B1 | 5/2001 |
| EP | 1120394 B1 | 9/2004 |
| GB | 776282 A | 6/1957 |
| JP | 2003306603 A | 10/2003 |
| JP | 2006-016548 A † | 1/2006 |
| WO | 0110812 A1 | 2/2001 |
| WO | 17006217 A1 | 1/2017 |
| WO | 18007356 A1 | 1/2018 |

OTHER PUBLICATIONS

International Search report PCT/EP2020/051845 dated Mar. 2, 2020 (pp. 1-3).

† cited by third party

*Primary Examiner* — Terressa Boykin
(74) *Attorney, Agent, or Firm* — Millen, White, Zelano & Branigan, P.C.; Csaba Henter

(57) ABSTRACT

A process for the production of a terephthalate polyester, containing a stage a) for preparing an esterification feedstock containing at least one mixing section fed with at least one terephthalic acid feedstock and one diester monomer feedstock, where the ratio of the total number of moles of diol units with respect to the total number of moles of terephthalate units introduced into the mixing section is between 1.0 and 2.0, the mixing section being operated at a temperature between 25° C. and 250° C. and at a pressure greater than or equal to 0.1 MPa, an esterification stage b) to produce at least one reaction effluent and one aqueous effluent, a polycondensation stage c) to obtain at least the terephthalate polyester and an effluent containing at least one diol monomer, and a stage d) of treatment of the diols to obtain a purified diol stream.

12 Claims, No Drawings

PROCESS FOR THE PRODUCTION OF A TEREPHTHALATE POLYESTER FROM A MONOMER MIXTURE COMPRISING A DIESTER

TECHNICAL FIELD

The invention relates to a process for the production of a polyester, in particular of a terephthalate polyester, such as polyethylene terephthalate (PET), from a mixture comprising at least terephthalic acid, and a diester of terephthalic acid and of a diol. The said diester is preferably a diester resulting from a process of recycling of polyester material, that is to say a diester obtained at the end of a process for the depolymerization of a polyester material to be recycled.

PRIOR ART

The chemical recycling of polyester, especially of polyethylene terephthalate (PET), has formed the subject of numerous research studies targeted at breaking down the polyester recovered in the form of waste into monomers which will again be able to be used as feedstock for a polymerization process.

Numerous polyesters are produced by circuits for collecting and sorting materials. In particular, the polyester, especially PET, can originate from the collecting of bottles, containers, films, resins and/or fibres composed of polyester (such as, for example, textile fibres, tyre fibres). The polyester resulting from collecting and sorting industries is known as polyester to be recycled.

PET to be recycled can be classified into four main categories:
  clear PET, predominately composed of uncoloured transparent PET (generally at least 60% by weight) and azure coloured transparent PET, which does not contain pigments and can be charged to mechanical recycling processes;
  dark or coloured (green, red, and the like) PET, which can generally contain up to 0.1% by weight of dyes or pigments but remains transparent or translucent;
  opaque PET, which contains a significant amount of pigments at contents typically varying between 0.25% and 5.0% by weight, in order to opacify the polymer. Opaque PET is increasingly being used, for example in the manufacture of food containers, such as milk bottles, in the composition of cosmetic, plant-protection or dye bottles;
  multilayer PET, which comprises layers of polymers other than PET or a layer of recycled PET between layers of virgin PET (that is to say, PET which has not been subjected to recycling), or a film of aluminium, for example. Multilayer PET is used, after thermoforming, to produce packagings, such as containers.

The collecting industries which make it possible to supply the recycling industries are structured differently depending on the country. They are changing so as to maximize the amount of plastic recovered in value from the waste as a function of the nature and of the amount of the streams and of the sorting technologies. The industry for recycling these streams generally consists of a first stage of conditioning in the form of flakes during which bales of raw packaging are washed, purified and sorted, ground and then again purified and sorted to produce a stream of flakes generally containing less than 1% by weight of "macroscopic" impurities (glass, metals, other plastics, wood, paper, board, inorganic elements), preferentially less than 0.2% of "macroscopic" impurities and more preferentially still less than 0.05%.

Clear PET flakes can subsequently be subjected to an extrusion-filtration stage which makes it possible to produce extrudates which can subsequently be reused as a mixture with virgin PET to produce new products (bottles, fibres, films). A stage of solid state polymerization under vacuum (known under the acronym SSP) is necessary for food uses. This type of recycling is known as mechanical recycling.

Dark (or coloured) PET flakes can also be recycled mechanically. However, the colouration of the extrudates formed from the coloured streams limits the uses: dark PET is generally used to produce packaging strips or fibres. The outlets are thus more limited in comparison with those of clear PET.

The presence of opaque PET containing pigments at high contents, in the PET to be recycled, presents problems to recyclers as opaque PET detrimentally affects the mechanical properties of recycled PET. Opaque PET is currently collected with coloured PET and is found in the coloured PET stream. In view of the development of uses for opaque PET, contents of opaque PET in the stream of coloured PET to be recycled are currently between 5-20% by weight and are tending to increase further. In a few years time, it will be possible to achieve contents of opaque PET in the coloured PET stream of greater than 20-30% by weight. In point of fact, it has been shown that, above 10-15% of opaque PET in the coloured PET streams, the mechanical properties of the recycled PET are detrimentally affected (cf. *Impact du développement du PET opaque blanc sur le recyclage des emballages en PET* [Impact of the growth of white opaque PET on the recycling of PET packagings], preliminary report of COTREP of May 12, 2013) and prevent recycling in the form of fibres, the main outlet of the industry for coloured PET.

Dyes are natural or synthetic substances which are soluble, in particular in the polyester material, and are used to colour the material into which they are introduced. The dyes generally used have different natures and often contain heteroatoms of 0 and N type, and conjugated unsaturations, such as, for example, quinone, methine or azo functional groups, or molecules such as pyrazolone and quinophthalone. Pigments are finely divided substances which are insoluble, in particular in the polyester material, and which are used to colour and/or opacify the material into which they are introduced. The main pigments used to colour and/or opacify polyesters, in particular PET, are metal oxides, such as $TiO_2$, $CoAl_2O_4$ or $Fe_2O_3$, silicates, polysulfides and carbon black. The pigments are particles with a size generally of between 0.1 and 10 μm and predominantly between 0.4 and 0.8 μm. The complete removal of these pigments by filtration, which is necessary in order to envisage recycling the opaque PET, is technically difficult as they have an extremely high clogging capability.

The recycling of coloured and opaque PETs is thus extremely problematic.

The improvement in the process for the polymerization of PET has also formed the subject of numerous research studies. Some of these research studies relate to the improvement in the phase of preparation of the mixture of the monomers, originating or not originating from the recycling industry.

In particular, Patent Application MX 2007/004429 discloses the production of a polyester of good quality, comprising a process for the depolymerization by glycolysis at atmospheric pressure of PET flakes in the presence of ethylene glycol in a bis(2-hydroxyethyl) terephthalate (BHET) base. The intermediate product obtained at the end of the depolymerization stage is filtered through a sintered system in order to retain particles of at least 25 µm before being introduced into the polymerization reactor, in order to obtain a polyester of good quality. However, the document MX 2007/004429 does not disclose the addition of terephthalic acid with its intermediate into the polymerization reactor.

Patent Application US 2006/0074136 describes a process for the depolymerization by glycolysis of coloured PET, in particular resulting from the recovery of green-coloured PET bottles. The BHET stream obtained at the end of the glycolysis stage is purified through active carbon in order to separate certain dyes, such as blue dyes, and then by extraction of the residual dyes, such as yellow dyes, by an alcohol or by water. The BHET, which crystallizes from the extraction solvent, is then separated, for the purpose of being able to be used in a PET polymerization process. In Patent Application US 2015/0105532, post-consumption PET, comprising a mixture of different coloured PETs, such as clear PET, blue PET, green PET and/or amber PET, is depolymerized by glycolysis in the presence of an amine catalyst and of alcohol. The diester monomer then obtained can be purified by filtration, ion exchange and/or by passing through active carbon, before being crystallized and recovered by filtration in order to be polymerized and to thus reform a polyester. These two patent applications do not, however, describe in detail the stages of the (re)polymerization process.

Patent Application WO 2017/006217 discloses the process for the preparation of a glycol-modified polyethylene terephthalate (r-PETG) comprising a stage of depolymerization of a PET in the presence of a mixture of monoethylene glycol (MEG) and of neopentyl glycol, followed directly by a stage of polymerization of the reaction effluent.

Patent Application FR 3 053 691 describes a process for the depolymerization of a polyester feedstock especially comprising from 0.1% to 10% by weight of pigments, by glycolysis in the presence of ethylene glycol. An effluent of bis(2-hydroxyethyl) terephthalate (BHET) monomers, which is obtained after specific separation and purification stages, can feed a stage of polymerization for the purpose of producing PET, without any condition being specified.

Patent JP3715812 describes the production of refined BHET from PET, it being possible for the BHET obtained to be used as starting material in a process for the production of plastic products. In the same way, Patent EP 1 120 394 discloses the optional use, as starting material for the reproduction of a high-quality polyester, of high-purity bis(2-hydroxyethyl) terephthalate. For this, Patent EP 1 120 394 more particularly describes a process for the depolymerization of a polyester without describing in detail the downstream stages of polymerization.

Patent U.S. Pat. No. 4,001,187 discloses processes for the production of high-quality PET, comprising a stage of continuously feeding ethylene glycol and terephthalic acid into the esterification medium comprising bis(2-hydroxyethyl) terephthalate, the amounts of acid and of diol introduced depending on a parameter related to the viscosity of the mixture (slurry). Patent U.S. Pat. No. 6,815,525 discloses a process for the production of PET, comprising a stage of continuously feeding recycled ethylene glycol into the reaction medium. Patent U.S. Pat. No. 4,334,090 for its part describes in detail a process for the preparation of the slurry, the viscosity of which is improved by incorporation of terephthalic acid crystals pretreated by attrition. None of these documents provides a process for the production of polyester with an improvement in the mixture of terephthalic acid and diol monomers, making it possible to reduce the solids content of the said mixture and thus to facilitate the subsequent operations, in particular of transportation, and to reduce the consumption of starting materials, in particular of diol.

SUMMARY OF THE INVENTION

A subject-matter of the invention is a process for the production of a terephthalate polyester, comprising:

a) a stage for preparing an esterification feedstock, comprising at least one mixing section that is fed with at least one terephthalic acid feedstock and one diester monomer feedstock, wherein the amounts of at least the said terephthalic acid feedstock and the said diester monomer feedstock, introduced into the said mixing section in the said mixture, are adjusted so that the ratio of the total number of moles of diol units of formula —[$C_{(n+1)}H_{(2n+2)}O_2$]—, n being an integer greater than or equal to 1, introduced into the said mixing section, with respect to the total number of moles of terephthalate units of formula —[$CO$—($C_6H_4$)—$CO$]—, introduced into the said mixing section, is between 1.0 and 2.0, wherein the said mixing section is operated at a temperature of between 25° C. and 250° C. and at a pressure of greater than or equal to 0.1 MPa, b) a stage for esterifying the said esterification feedstock resulting from stage a), in order to produce at least one reaction effluent and one aqueous effluent, wherein the said esterification stage comprises at least one reaction section, operated at a temperature between 150° C. and 400° C., at a pressure between 0.05 and 1 MPa, and with a residence time between 1 and 10 h, and at least one separation section, c) a stage of polycondensation of the said reaction effluent obtained in stage b) in order to obtain at least the said terephthalate polyester and a diol effluent, the said stage comprising at least one reaction section comprising at least one reactor in which the polycondensation is carried out and which is operated at a temperature between 200° C. and 400° C., at a pressure between 0.0001 and 0.1 MPa, with a residence time between 0.1 and 5 h, the said reaction section also comprising at least one withdrawal of a diol effluent, d) a stage for treating the diols, comprising a recovery section that is fed at least with all or part of the diol effluent resulting from stage c), in order to obtain a diol effluent to be treated, and a section for purifying the said diol effluent to be treated, in order to obtain a purified diol stream.

Preferably, the present invention relates to a process for the production of a terephthalate polyester from at least one polyester feedstock to be recycled consisting of the stages a), b), c) and d) described above.

One advantage of the invention lies in the optimized preparation of the monomer feedstock. This is because the present invention makes possible the replacement that is at least partial, by a terephthalic diester compound, of the monomers feedstocks, that is to say of terephthalic acid and of diol, of the conventional processes for producing terephthalic polyesters.

Thus, the present invention has the advantage of preparing a monomer feedstock exhibiting a reduced solids content, with respect to the mixtures of the monomers feedstocks of the conventional processes for producing terephthalate polyester in which no diester monomer is incorporated, the solids content being a solids content by volume defined, according to the invention, as the ratio of the volume of solids to the total volume of the two-phase monomer feedstock (that is to say, of the esterification feedstock according to the invention). The present invention thus makes it possible to facilitate the operations of preparation and of transportation of the two-phase mixture, in particular during the polyester production process.

Another advantage of the present invention is the decrease in the amount of diol monomer introduced into the polyester production process, in comparison with the conventional polyester production processes, while retaining the operability of the preparation stage, that is to say without damaging the preparation conditions or the quality of the mixture of the monomers feedstocks. As the amount of diol introduced in excess into the process is decreased, the amount of diol recovered, treated and recycled at the end of polymerization is thus decreased, inducing, besides the reduction in consumption of diol starting material, a reduction in the energy consumption of the process.

Furthermore, when the diester monomer incorporated in the mixture is advantageously a liquid diester intermediate obtained at the end of a polyester depolymerization process, the said intermediate corresponding to the specifications of the polymerization process is directly incorporated in the mixture of stage a), without additional stage of purification and/or of intermediate conditioning (for example a stage of solidification of the diester obtained by depolymerization of the polyester), thus limiting, inter alia, significant consumptions of energy and thus meeting an ecological expectation of society.

DESCRIPTION OF THE EMBODIMENTS

The invention relates to a process for producing a terephthalate polyester comprising in particular a stage for preparing a specific polymerization feedstock.

According to the invention, the terms "polyester" and "terephthalate polyester" are interchangeable and denote a polyalkylene terephthalate. Very conventionally, a polyalkylene terephthalate is the result of the polycondensation of a diol (or glycol) monomer with a terephthalic acid (or dimethyl terephthalate) monomer. The terephthalate polyester according to the invention is especially polyethylene terephthalate (PET), polybutylene terephthalate (PBT), polytrimethylene terephthalate (PTT) or any other polymer, the repeating unit of the main chain of which contains an ester functional group and an aromatic ring resulting from terephthalic acid (or from one of its esters, especially dimethyl terephthalate). According to the invention, the preferred terephthalate polyester is polyethylene terephthalate or poly(ethylene terephthalate), also known simply as PET, the basic repeating unit of which exhibits the following formula:

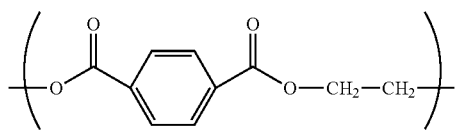

Conventionally, PET is obtained by polycondensation of terephthalic acid (PTA) or dimethyl terephthalate (DMT) with ethylene glycol.

According to the invention, the expression "to be recycled" describes any material, especially comprising polyester, resulting from industries for collecting and sorting plastic waste. In contrast, a virgin polyester results solely from the polymerization of monomer feedstocks comprising at least one dicarboxylic acid (for example terephthalic acid, PTA) or one dicarboxylic ester (for example dimethyl terephthalate, DMT) and at least one compound of the family of the diols or glycols (for example ethylene glycol).

According to the invention, the term "diester monomer" denotes a terephthalate ester compound of chemical formula $HOC_{(m+1)}H_{(2m+2)}-CO_2-(C_6H_4)-CO_2-C_{(n+1)}H_{(2n+2)}OH$, in which: $-(C_6H_4)-$ represents an aromatic ring; n and m are integers which are identical or different, preferably identical (that is to say, n=m), and greater than or equal to 1, preferably of between 1 and 5, preferably of between 1 and 3. A molecule of diester monomer corresponds to a compound which would result from the esterification of one molecule of terephthalic acid $HOOC-(C_6H_4)-COOH$ (where $-(C_6H_4)-$ represents an aromatic ring) with two molecules of at least one diol (or glycol), more particularly with a molecule of a diol of chemical formula $HO-C_{(n+1)}H_{(2n+2)}-OH$ and a molecule of a diol of chemical formula $HO-C_{(m+1)}H_{(2m+2)}-OH$. The preferred diester monomer is bis(2-hydroxyethyl) terephthalate (BHET). According to the invention, the "diester monomer feedstock" comprises a diester monomer as defined above. The "diester monomer feedstock" according to the invention can also comprise at least one diol (or glycol), preferably corresponding to the diol unit(s) present in the said diester monomer of the said feedstock. Advantageously, the said diester monomer feedstock preferably comprises at least 10% by weight of diester monomer, preferentially at least 20% by weight.

The term "dye" is understood to mean a substance which is soluble in the polyester material and which is used to colour it. The dye can be of natural or synthetic origin.

The term "pigment", more particularly colouring and/or opacifying pigment, is understood to mean a finely divided substance which is insoluble in the polyester material. The pigments are in the form of particles with a size generally of between 0.1 and 10 μm and predominantly between 0.4 and 0.8 μm. They are often of inorganic nature. Conventionally, the pigments, in particular opacifying pigments, used are metal oxides, such as $TiO_2$, $CoAl_2O_4$ or $Fe_2O_3$, silicates, polysulfides and carbon black.

According to the present invention, the expression "between . . . and . . . " means that the limiting values of the interval are included in the range of values which is described. If such were not the case and if the limiting values were not included in the range described, such an accuracy will be given by the present invention.

Feedstocks

In accordance with the invention, the said process is fed with at least one terephthalic acid feedstock and one diester monomer feedstock.

The terephthalic acid feedstock is advantageously in the powder form, that is to say in the form of solid terephthalic acid particles. The terephthalic acid particles incorporated in the mixture of monomers preferably exhibit a mean diameter preferably of between 1 and 1000 μm, especially between 30 and 500 μm and in particular between 80 and 200 μm. The mean diameter of the terephthalic acid particles is determined by any method of particle size analysis known to a person skilled in the art, such as, for example, by laser diffraction or by sieving, preferably by sieving on a column of suitable sieves according to a technique known to a person skilled in the art.

The terephthalic acid of the terephthalic acid feedstock can advantageously be produced by oxidation of para-xylene or by depolymerization of polyesters or by any other process which makes it possible to obtain a terephthalic acid feedstock with the specifications required by the polymerization processes. The terephthalic acid can result from fossil hydrocarbon sources or from biomass.

According to the invention, the diester monomer feedstock comprises a diester monomer, as defined above, corresponding to a terephthalate diester compound of chemical formula $HOC_{(m+1)}H_{(2m+2)}\text{—}CO_2\text{—}(C_6H_4)\text{—}CO_2\text{—}C_{(n+1)}H_{(2n+2)}OH$, in which: —$(C_6H_4)$— represents an aromatic ring; n and m are integers which are identical or different, preferably identical (that is to say, n=m), and greater than or equal to 1, preferably of between 1 and 5, preferably of between 1 and 3. The diester monomer preferably comprises the basic repeating units of the terephthalate polyester produced by the process according to the invention. Very preferentially, the diester monomer feedstock comprises bis(2-hydroxyethyl) terephthalate (BHET), as diester monomer. The diester monomer feedstock according to the invention can also comprise at least one diol, preferably corresponding to the diol unit(s) present in the said diester monomer of the said feedstock. The said diester monomer feedstock preferably comprises at least 10% by weight of diester monomer, preferentially at least 20% by weight. According to the invention, the diester monomer feedstock can be in the liquid form or in the solid form; preferably, the diester monomer feedstock is in the liquid form.

In an advantageous embodiment of the invention, the said diester monomer feedstock of stage a) comprises at least a fraction, preferably comprises all, of a purified diester effluent, obtained at the end of a process for the depolymerization of a polyester feedstock to be recycled, especially obtained at the end of the processes for the depolymerization of a polyester feedstock to be recycled of Patents JP 3715812 and FR 3053691 and of Application WO 01/10812.

Advantageously, the said purified diester effluent is obtained by a process for the depolymerization of a polyester feedstock to be recycled comprising at least the following stages:
  i) a depolymerization stage comprising at least one reaction section that is fed with the said polyester feedstock to be recycled and with a glycol stream, in order to obtain a depolymerization reaction effluent,
  ii) a separation/purification stage comprising a separation section, in order to obtain a glycol effluent, and at least one purification section, in order to obtain a purified diester effluent; at least a fraction of the said purified diester effluent obtained in stage ii) is sent to the said stage a).

In this embodiment, the said polyester feedstock to be recycled results from the industries for collecting and sorting waste, in particular plastic waste. Preferably, the said polyester feedstock to be recycled is a polyethylene terephthalate PET feedstock to be recycled.

The polyester feedstock to be recycled which feeds the depolymerization stage i) can be in the form of flakes, the greatest length of which is less than 10 cm, preferentially between 5 and 25 mm, or in micronized solid form, that is to say in the form of particles preferably having a size of between 10 microns and 1 mm. The polyester feedstock to be recycled preferably comprises less than 2% by weight, preferentially less than 1% by weight, of "macro" impurities, such as waste formed of glass, metal, plastic, other than terephthalate polyester, wood, paper, board or inorganic elements. The said polyester feedstock to be recycled can also be in the form of fibres, such as textile fibres, optionally pretreated in order to remove cotton or polyamide fibres or any other textile fibre other than polyester fibre, or such as tyre fibres, optionally pretreated in order to remove in particular polyamide fibres or rubber or polybutadiene residues. The said polyester feedstock to be recycled, which feeds the depolymerization stage i), advantageously contains more than 50% by weight of polyalkylene terephthalate, preferably more than 70% by weight, in a preferred way more than 90% by weight, of polyalkylene terephthalate.

The said polyester feedstock to be recycled can be obtained from clear, coloured, opaque, dark and/or multilayer terephthalate polyester, preferably PET, waste. It advantageously comprises at least one opaque, dark or multilayer terephthalate polyester, preferably PET. Preferably, it comprises at least 10% by weight of opaque terephthalate polyester, preferably of opaque PET, very preferably at least 15% by weight of opaque terephthalate polyester, preferably of PET. The said polyester feedstock to be recycled can contain up to 10% by weight of pigments, especially between 0.1% and 10% by weight of pigments, in particular between 0.1% and 5% by weight of pigments, and/or up to 1% by weight of dyes, especially between 0.05% and 1% by weight of dyes, in particular between 0.05% and 0.2% by weight of dyes.

The said polyester feedstock to be recycled can also contain elements used as polymerization catalyst and/or as stabilizing agents in polyester production processes, such as antimony, titanium or tin.

Advantageously, the depolymerization stage i) employs, in the reaction section, a reaction for the glycolysis of the polyalkylene terephthalate of the said polyester feedstock to be recycled, in the presence of the said glycol stream, in one or more reactors. The said glycol stream preferably comprises a diol monomer which corresponds to the diol unit in the composition of the basic repeating unit of the terephthalate polyester produced by the production process according to the invention. Preferably, the said glycol stream is an ethylene glycol stream. Advantageously, the said glycol stream which feeds the depolymerization stage i) comprises, preferably consists of, at least a fraction of the said purified diol stream obtained at the end of stage d) of the process for the production of the terephthalate polyester according to the invention.

The said reaction section of the depolymerization stage i) is carried out at a temperature of between 150° C. and 400° C., preferably between 180° C. and 300° C., in a preferred way between 200° C. and 280° C., at an operating pressure of at least 0.1 MPa, preferentially at least 0.4 MPa, and with a residence time per reactor of between 0.05 and 10 h, preferably between 0.1 and 6 h, in a preferred way between 0.5 and 4 h, the said residence time per reactor being defined as the ratio of the liquid volume of the reactor to the flow rate by volume of the stream which feeds the said reactor. The glycol stream feeds the reaction section so that the amount of the glycol compound contained in the said glycol stream is adjusted to from 1 to 20 moles of the diol of the said glycol stream per mole of basic repeating unit of the polyester contained in the said polyester feedstock to be recycled, preferably from 3 to 10 moles of diol of the said glycol stream per mole of diester in the said polyester feedstock to be recycled.

The depolymerization reaction can be carried out with or without addition of a catalyst. When the depolymerization reaction is carried out after addition of a catalyst, the latter can be homogeneous or heterogeneous and chosen from the esterification catalysts known to a person skilled in the art, such as complexes, oxides and salts of antimony, tin or titanium, alkoxides of metals from Groups (I) and (IV) of the Periodic Table of the Elements, organic peroxides or acidic/basic metal oxides. Preferably, the depolymerization reaction is carried out without addition of catalyst.

The depolymerization reaction can also advantageously be carried out in the presence of a solid adsorbing agent in the powder or shaped form, the role of which is to capture at least a part of the impurities, in particular of the coloured impurities, thus relieving the strain on the purification phase of stage ii). The said solid adsorbing agent is especially an activated carbon.

The depolymerization reaction effluent obtained at the end of the depolymerization stage i) comprises a mixture of diester monomers, of oligomers comprising between 1 and 5, preferably between 1 and 3, basic units of formula —[O—CO—($C_6H_4$)—CO—O-$C_{(n+1)}H_{(2n+2)}$]—, with, n an integer of between 1 and 5, preferably between 1 and 5, of diol compounds, of impurities possibly present in the said polyester feedstock and of compounds possibly produced at the end of side reactions, such as, for example, etherification or decomposition reactions. The diol compounds are advantageously diol monomers and comonomers participating in the composition of the polyester feedstock to be recycled and released at the end of the depolymerization reaction and those, unreacted, resulting from the glycol stream feeding the depolymerization stage i). The said depolymerization reaction effluent can also contain unconverted polyesters and other polymers.

The depolymerization reaction effluent obtained at the end of the depolymerization stage i) feeds the separation/purification stage ii) which comprises at least one section for separation of a glycol effluent and at least one purification section, in order to obtain a purified diester effluent.

The said separation and purification sections can be in one order or another with respect to each other. The said separation and purification sections can also be interconnected when stage ii) comprises a section for purification of the depolymerization reaction effluent, in order to obtain a purified depolymerization reaction effluent, a section for separation of the said purified depolymerization reaction effluent, in order to obtain a glycol effluent and a diester effluent, and a section for purification of the said diester effluent, in order to obtain a purified diester effluent.

In a preferred embodiment, stage ii) comprises a section for separation of the said depolymerization reaction effluent in order to obtain a glycol effluent, advantageously comprising the unreacted diol of the glycol stream of stage i), and a diester effluent, and a section for purification of the said diester effluent, in order to obtain a purified diester effluent. The said glycol effluent obtained at the outlet of the separation section of stage ii) advantageously comprises more than 50% by weight, preferably more than 70% by weight, in a preferred way more than 90% by weight, of diols. The said separation section advantageously makes it possible to recover the unreacted diol of the glycol stream of stage i). The said diester effluent obtained at the outlet of the separation section is preferably in the liquid form and advantageously comprises more than 10% by weight, preferably more than 25% by weight, in a preferred way more than 50% by weight, of diester monomers and oligomers.

Advantageously, the said separation section comprises one or more separation devices, in order to make possible the recovery of an effluent enriched in diols (the glycol effluent) and optionally of an effluent enriched in light impurities and of an effluent enriched in heavy impurities. Any physical, chemical or physical/chemical separation method known to a person skilled in the art can be used, such as, for example, gas/liquid separation, distillation, evaporation, extraction by solvent, coupled or not coupled with a chemical reaction, crystallization followed by a filtration or centrifugation or a combination of the said separation methods. Preferably, the said separation section comprises a sequence of gas/liquid separations, preferably from 1 to 5 gas/liquid separations, carried out at a temperature of between 100 and 250° C., preferably between 110 and 220° C., in a preferred way between 120 and 210° C., and at a pressure of between 0,00001 and 0.2 MPa, preferably between 0.00004 and 0.15 MPa, in a preferred way between 0.00004 and 0.1 MPa.

Preferably, all or part of the said glycol effluent recovered on conclusion of stage ii) is advantageously sent to the treatment stage d) of the process according to the invention.

All or part of the said glycol effluent recovered at the end of stage ii) can be prepurified in a section for prepurification of the diols included in stage ii) in order to remove a part of the impurities entrained with the said glycol effluent, such as, for example, dyes, pigments or other solid particles. The prepurification section fed with all or part of the said glycol effluent can comprise, non-exhaustively, an adsorption on a solid (for example on active carbon) and a filtration system. At least a fraction of the said prepurified glycol effluent can be directly recycled to the depolymerization stage i). A separation of the different diols possibly included in the said glycol effluent can be carried out in the said prepurification section.

The phase of purification of the diester effluent consists in separating at least one purified diester monomer effluent from all or part of the following compounds resulting from the depolymerization stage i): diester oligomers, possibly unconverted polyester, impurities possibly present in the polyester feedstock to be recycled, such as other polymers, pigments, dyes, polymerization catalysts or any other inorganic compound making up the said polyester feedstock to be recycled or formed during the depolymerization stage i), while minimizing the loss of diester monomer.

The said diester effluent is advantageously purified by any physical, chemical or physical/chemical method known to a person skilled in the art which makes it possible to recover a purified diester monomer effluent with a yield of diester monomer of greater than or equal to 50% by weight, preferably of greater than or equal to 70% by weight, in a preferred way of greater than or equal to 80% by weight. The term "yield" is understood to mean the amount of diester monomer in the said purified diester monomer stream with respect to the total amount of diester monomer introduced into the purification section. Preferably, the said purified diester monomer effluent is devoid of dyes or of inorganic impurities, such as pigments, depolymerization catalysts and ions. Preferably, the purified diester monomer comprises the molecules of diester monomer and possibly of the oligomers of the said diester with a degree of polymerization of between 2 and 5.

The purification of the said diester effluent (and/or of the said depolymerization reaction effluent) advantageously employs one or more purification operations, such as filtration, evaporation, distillation, membrane separation, precipitation or crystallization, adsorption on a trapping mass, treatment on an ion-exchange resin or extraction by a solvent. For example, in Patent EP 0 865 464, the purification of the diester effluent comprises a sequence of dissolution operation in a hot solvent, then precipitation and filtration, in order to separate the impurities with a size of greater than 50 μm, and the separation of the diester monomers and the oligomers in a thin film evaporator. Optionally, the purification section of stage ii) can comprise at least two purification operations (or phases):

- a first purification phase which makes possible the separation of impurities which are insoluble in the said diester effluent (and/or the said depolymerization reaction effluent) or which have become insoluble after cooling or partial evaporation of the said effluent or addition of a third body, such as, for example, a flocculating agent or solvent which promotes precipitation;
- a second purification phase which makes possible the separation of impurities which are soluble in the said diester effluent (and/or the said depolymerization reaction effluent) or which have become soluble after heating or addition of a solvent.

Preferably, the purification of the said diester effluent (and/or of the said depolymerization reaction effluent) employs a separation section comprising a falling film or thin film evaporation system, or a short path falling film or thin film distillation, or a sequence of several short path falling film or thin film evaporations and/or distillations, operated at a temperature of less than or equal to 250° C., preferably of less than or equal to 230° C., preferentially of less than or equal to 200° C., and at a pressure of less than or equal to 0.001 MPa, preferably of less than or equal to 0.0001 MPa, in a preferred way of less than or equal to 0.00005 MPa, then a decolouration section operated at a temperature between 100 and 250° C., preferably between 110 and 200° C. and in a preferred way between 120 and 180° C., and at a pressure between 0.1 and 1.0 MPa, preferably between 0.2 and 0.8 MPa and in a preferred way between 0.3 and 0.5 MPa, in the presence of an adsorbent, preferably an active carbon.

Advantageously, the purified diester effluent obtained at the end of stage ii) comprises at least 10% by weight of diester monomer, preferably at least 20% by weight of diester monomer. It preferably contains less than 1% by weight, preferably less than 0.1% by weight, of the pigments introduced into the process with the polyester feedstock to be recycled and less than 10% by weight, preferably less than 1% by weight, of the dyes introduced into the process with the polyester feedstock to be recycled.

The said stage ii) can also produce an effluent of ester impurities composed of oligomers and optionally of polymers not converted in the depolymerization stage i). The said effluent of ester impurities can advantageously be completely or partially recycled to stage i) or bled off and sent to an incineration system. If appropriate, the said fraction of the said effluent of ester impurities recycled to stage i) can be subjected to at least one separation operation, preferably a filtration operation, so as to reduce the amount of pigments and/or other solid impurities possibly present in the said effluent of ester impurities. Optionally, all or part of at least a fraction of the glycol effluent resulting from stage ii) or from stage d) of the process according to the invention can advantageously be mixed with the said recycled fraction of the effluent of ester impurities so as to reduce the viscosity of the said fraction of the said effluent of ester impurities and to make it easier to transport it to stage i) and optionally to make it easier to treat it in an optional filtration stage.

Preferably, the purified diester effluent is recovered at the end of stage ii) in the liquid form or in the solid form, preferably in the liquid form.

Advantageously, at least a fraction of the said purified diester effluent obtained in stage ii) is sent to stage a) of the process for the production of a terephthalate polyester according to the invention.

Stage a) of Preparation of the Esterification Feedstock

In accordance with the invention, the process for producing a terephthalate polyester comprises a stage a) of preparation of an esterification feedstock. The said stage a) comprises at least one mixing section that is fed with at least one terephthalic acid feedstock and one diester monomer feedstock.

The esterification feedstock, according to the invention, which is obtained at the end of stage a) is a homogeneous two-phase mixture comprising at least terephthalic acid, a diester monomer and optionally a diol (or glycol) of chemical formula HO—$C_{(n+1)}H_{(2n+2)}$—OH, n being an integer greater than or equal to 1, preferably between 1 and 5, in a preferred way between 1 and 3. The term "two-phase" is advantageously understood to mean a suspension of a solid phase in a liquid or pasty phase. The term "homogeneous" should be understood as meaning that the solid phase, in suspension in the liquid or pasty phase, is distributed in a homogeneous way throughout the liquid or pasty phase. More particularly, the esterification feedstock according to the invention is a mixture of solid terephthalic acid particles, with a diameter typically of between 1 and 1000 μm, in particular between 80 and 300 μm, homogeneously distributed in a liquid or pasty phase comprising the diol monomers and the diester monomers.

Advantageously, the amounts of the monomer feedstocks, that is to say the amount of at least the terephthalic acid feedstock and the diester monomer feedstock, which are introduced into the said mixing section, are adjusted so that the ratio of the total number of moles of diol units of formula —$[C_{(n+1)}H_{(2n+2)}O_2]$—, n being an integer greater than or equal to 1, introduced into the said mixing section, with respect to the total number of moles of terephthalate units of formula —[CO—($C_6H_4$)—CO]— introduced into the said mixing section, is between 1.0 and 2.0, preferably between 1.0 and 1.5, in a preferred way between 1.0 and 1.3.

Preferably, the mixing section of stage a) is fed with diester monomer feedstock in the liquid form. When the diester monomer feedstock intended to feed the mixing section is in the solid form, stage a) of the process of the invention can optionally comprise a conditioning section, located upstream of the mixing section, in order to obtain a liquid diester monomer feedstock. The said optional conditioning section is at least fed with the diester monomer feedstock in the solid form and operated at a temperature greater than the liquefaction temperature of the said diester monomer feedstock, preferably of between 25° C. and 250° C., and at a pressure of greater than or equal to 0.1 MPa. The pressure of the said mixing section is very advantageously less than or equal to 5 MPa.

In a preferred embodiment of the invention, the said mixing section of the said stage a) of the process according to the invention is additionally fed with a diol monomer feedstock, preferably comprising a diol monomer corresponding to the diol unit(s) contained in the diester monomer of the said diester monomer feedstock. It predominantly comprises the diol monomer which participates in the composition of the basic repeating unit of the terephthalate polyester produced by the process according to the invention. Preferably, the diol monomer feedstock comprises at least 70 mol %, preferentially at least 90 mol %, very preferably 99.5 mol %, of a diol monomer participating in the composition of the individual unit of the targeted terephthalate polyester. Preferably, the diol monomer feedstock comprises ethylene glycol. The said diol monomer feedstock is preferably in the liquid form.

Preferably, the said diol monomer feedstock can be, at least in part, a fraction of the purified diol stream obtained in stage d) of the process according to the invention. The said diol monomer feedstock can optionally comprise an external diol source.

When a diol monomer feedstock is incorporated in the mixing section of stage a), the amount of the said diol feedstock introduced into the mixing section of stage a) is adjusted so that the ratio of the number of diol units with respect to the number of terephthalate units in the mixture of stage a), as defined above, is between 1.0 and 2.0, preferably between 1.0 and 1.5 and in a preferred way between 1.0 and 1.3.

Advantageously, the amount of molecules of diester monomer contained in the diester monomer feedstock introduced into the mixing section of stage a) represents at least 5% by weight, with respect to the weight of terephthalic acid (PTA), preferably at least 15% by weight.

A molecule of diester monomer of the diester monomer feedstock comprises two diol units and one terephthalate unit. A terephthalic acid molecule comprises one terephthalate unit. A diol molecule comprises one diol unit. Thus, the incorporation of one mole of diester monomer, for example one mole of bis(2-hydroxyethyl) terephthalate (BHET), as a mixture with the terephthalic acid monomer and diol monomer feedstocks, preferably a diol corresponding to the diol unit contained in the said diester monomer, such as ethylene glycol, makes it possible to replace a part of the said terephthalic acid feedstock and all or part of the said diol feedstock.

Advantageously, the said mixing section in stage a) of the process according to the invention is operated at a temperature of between 25 and 250° C., preferably between 60 and 200° C., in a preferred way between 100 and 150° C., and at a pressure of greater than or equal to 0.1 MPa. The pressure of the said mixing section is very advantageously less than or equal to 5 MPa.

One or more polymerization catalysts can, in addition, be incorporated in the mixture of stage a) of the process according to the invention.

Other monomer (or comonomer) compounds can also advantageously be introduced into the mixture and be found in the esterification feedstock. Non-exhaustively, the said other monomer compounds can be dicarboxylic acids, such as, for example, isophthalic acid, and diols, such as, for example, 1,4-dihydroxymethylcyclohexane and diethylene glycol.

The process according to the invention, by incorporating a diester monomer, for example BHET monomers, in the esterification feedstock, thus makes it possible to replace a part of the terephthalic acid, which is a compound in the form of a powder of solid particles, in the two-phase mixture of the monomers for the production of polyester. The solids content of this two-phase mixture can thus be reduced, with respect to conventional processes for the production of polyester, thus facilitating the subsequent industrial operations, in particular its transportation. The presence of diester monomer, in particular of BHET, can also promote an increase in the rate of esterification of the terephthalic acid. The replacement of a part of the terephthalic acid and all or part of the diol by diester monomers, in the process according to the invention, also makes it possible, at an identical solids content of the two-phase reaction mixture with respect to that of the conventional polyester production processes, to reduce the amount of ethylene glycol introduced in excess into the mixture, bringing about a reduction in the costs, in particular of starting materials, but also a sizeable reduction in the energy consumption of the polyester production process, as a result of a greatly reduced amount of material to be treated and recycled.

Esterification Stage b)

In accordance with the invention, the process for the production of a terephthalate polyester comprises a stage b) of esterification of the esterification feedstock obtained at the end of stage a), in order to produce at least one reaction effluent and one aqueous effluent.

The said reaction effluent advantageously comprises diesters and ester oligomers. Preferably, the diesters in the said reaction effluent are of the same nature as the said diester monomer incorporated in the mixture of stage a). Preferably, the ester oligomers in the said reaction effluent are advantageously composed of the basic units corresponding to the basic repeating units of the terephthalate polyester produced by the process according to the invention.

Advantageously, the said esterification stage b) comprises at least one reaction section and at least one separation section, in order to separate the said reaction effluent and the said aqueous effluent.

The reaction carried out in stage b) advantageously comprises an esterification reaction which consists of a condensation reaction of at least the hydroxyl (—OH) groups of the diester monomer of the diester monomer feedstock incorporated in the esterification feedstock in stage a) and of the diol monomers optionally present in the esterification feedstock with at least the carboxyl (—COOH) groups of the terephthalic acid of the terephthalic acid feedstock incorporated in the esterification feedstock in stage a). This esterification reaction produces molecules of diester monomer, for example bis(2-hydroxyethyl) terephthalate (BHET), and diester oligomers advantageously comprising from 2 to 5 terephthalate units. It also releases water. The reaction carried out in stage b) of the process according to the invention also advantageously comprises transesterification reactions consisting of the condensation reaction of molecules of diester monomer with one another, thus releasing diol molecules.

The said reaction section is operated at a temperature between 150 and 400° C., preferably between 200 and 300° C., at a pressure between 0.05 and 1 MPa, preferably between 0.1 and 0.3 MPa, and with a residence time between 0.5 and 10 h, preferably between 1 and 5 h. According to the invention, the residence time in the said esterification stage b) is defined as the ratio of the reaction volume of a reactor of the said reaction section to the flow rate by volume of the liquid stream exiting from the said reactor. The esterification reaction is advantageously carried out in one or more stirred reactors in series or in parallel, in one or more tubular reactors in series or in parallel or in a combination of stirred and tubular reactors in series or in parallel.

The water formed during the esterification reaction is separated in the said separation section of stage b). Advantageously, the reaction section also comprises at least one withdrawal of a withdrawn effluent rich in water and in diol. The water is separated in particular by difference in volatility, for example by distillation, or by adsorption starting from the effluent withdrawn from the reaction medium containing at least a part of the diol and of the water released present in the reaction medium.

Advantageously, a polymerization catalyst known to a person skilled in the art, optionally as a mixture with a diol stream, feeds a finishing section of the esterification stage b).

The polymerization catalysts are non-exhaustively catalysts based on antimony, titanium, germanium or aluminium, acetate of zinc, calcium or manganese.

The incorporation of the diester monomer feedstock in the monomer feedstocks of the polymerization process according to the invention makes it possible to replace at least a part of the terephthalic acid feedstock and all or part of the diol feedstock, making it possible to reduce the amount of water formed and thus of effluent withdrawn from the reaction medium to be treated. The energy consumption is advantageously decreased thereby.

Polycondensation Stage c)

In accordance with the invention, the process for the production of a terephthalate polyester comprises a stage c) of polycondensation of the reaction effluent obtained in stage b), in order to obtain at least the said terephthalate polyester and a diol effluent. The said diol effluent comprises at least one diol monomer advantageously corresponding to the diol unit of formula —$[C_{(n+1)}H_{(2n+2)}O_2]$—, n being an integer greater than or equal to 1, included at least in the diester of the diester monomer feedstock which feeds the mixing section in stage a) of the process according to the invention.

The polycondensation stage c) consists in carrying out a condensation reaction between the diester monomers and oligomers obtained in the esterification stage b), in order to obtain a polyester with a given degree of polymerization and the desired physicochemical properties (for example: viscosity index, crystallinity, colour, mechanical properties, and the like). The said condensation reaction releases diol compounds, possibly water and coproducts, which it is advisable to remove.

The polycondensation c) stage comprises at least one reaction section comprising at least one reactor in which the polycondensation is carried out and at least one withdrawal of a diol effluent, advantageously comprising at least one monomer corresponding to the diol unit of formula —$[C_{(n+1)}H_{(2n+2)}O_2]$—, n being an integer greater than or equal to 1, included at least in the diester of the diester monomer feedstock which feeds the mixing section in stage a) of the process according to the invention.

Advantageously, the said reaction section is operated in one or more reactors, functioning in series or in parallel, at a temperature between 200 and 400° C., preferably between 250 and 300° C., at a pressure between 0.0001 and 0.1 MPa, preferably between 0.0004 and 0.01 MPa, with a residence time between 0.1 and 5 h, preferably between 0.5 and 3 h. According to the invention, the residence time in the said polycondensation stage c) is defined as the ratio of the reaction volume of a reactor of the said reaction section to the flow rate by volume of the liquid stream exiting from the said reactor. The condensation reaction in the polycondensation stage c) can be carried out in two successive reaction stages, a melt-phase condensation stage, followed by a solid-phase post-condensation stage.

Advantageously, polymerization additives and catalysts can be introduced the polycondensation stage c). Non-exhaustively, the additives can comprise agents which inhibit the etherification side reactions, such as, for example, amines (n-butylamine, diisopropylamine or triethylamine), sodium hydroxide or organic hydroxides or lithium carbonate, stabilizing agents, such as phosphites or phosphates, and compounds of polyamide type for reducing the amount of decomposition product, such as acetaldehyde. The polymerization catalysts commonly used are, such as, for example, catalysts based on antimony, titanium, germanium or aluminium, acetate of zinc, calcium or manganese.

Advantageously, the withdrawal of the said diol effluent is carried out using one or more withdrawal system(s), advantageously connected to the reactor(s) of the reaction section of the said stage c), and makes it possible to separate the diol monomer released during the condensation reaction and possibly the water and other coproducts possibly released during the condensation reaction. Preferably, the diol effluent, withdrawn from the reactor(s) of stage c), is a gaseous effluent which is subsequently advantageously cooled to a temperature between 0 and 100° C. and condensed in order to obtain an effluent in the liquid form, the said liquid effluent comprising at least the diol monomer.

Preferably, at least a fraction of the effluent comprising at least the diol monomer, preferably in the liquid form, is sent to stage d) of the process according to the invention.

Advantageously, the said effluent comprising at least the diol monomer, preferably in the liquid form, can be directly recycled, completely or partially, in the stage a) of preparation of an esterification feedstock.

In a very specific embodiment, the said effluent comprising at least the diol monomer, preferably in the liquid form, can be directly recycled, completely or partially, to the esterification stage b).

Stage d) of Treatment of the Diols

In accordance with the invention, the process for the production of a terephthalate polyester comprises a stage d) of treatment of the diols, comprising a recovery section fed at least with all or part of the diol effluent resulting from stage c), in order to obtain a diol effluent to be treated, and a section for purification of the said diol effluent to be treated, in order to obtain a purified diol stream.

Advantageously, the said recovery section of stage d) is fed at least with all or part of the diol effluent obtained in stage c), preferably in the liquid form. In addition, it can be fed with all or part of the glycol effluent resulting from the separation section of stage ii) of the process for the depolymerization of a polyester feedstock to be recycled, in the case of the advantageous embodiment of the invention in which the diester monomer feedstock of stage a) comprises at least a fraction of the purified diester effluent obtained at the end of the process for the depolymerization of a polyester feedstock to be recycled. Optionally, the said recovery section of stage d) of the process according to the invention can also be fed with an external contribution of diol. Advantageously, the recovery section can comprise one or more operations of filtration of the different streams comprising at least the diol monomer.

A diol effluent to be treated is obtained at the outlet of the recovery section of stage d) of the process according to the invention and is sent into the said purification section, in order to obtain a purified diol stream.

The said purification section comprises at least one separation system which makes it possible to carry out any method of physical, physicochemical or chemical separation known to a person skilled in the art, such as, for example, gas/liquid separation, distillation or adsorption. Preferably, the purification of the said diol effluent to be treated employs at least one distillation column, preferably a series of distillation columns, operated at a temperature between 50 and 250° C., preferably between 70 and 220° C., and at a pressure between 0.001 and 0.2 MPa, preferably between 0.01 and 0.1 MPa. Preferably, the said purification section comprises a phase of separation of the impurities which are lighter than the diol monomer of the diol effluent to be treated and a phase of separation of the impurities which are heavier than the diol monomer of the diol effluent to be treated, preferably in a series of distillation columns.

Advantageously, the said stage d) can also comprise a section for removal of the volatile organic compounds by thermal or catalytic combustion of the said compounds in order to prevent them from being discharged to the environment. Non-exhaustively, the said section for treatment of the impurities comprises a filtration if there are present solid particles and a catalytic or non-catalytic combustion system.

The process according to the invention thus makes it possible to obtain a terephthalate polyester, advantageously having the degree of polymerization targeted and the desired physicochemical properties, from an improved mixture of the monomers which makes it possible to limit the consumption of diol monomer and to reduce the amount of diol monomer possibly introduced, in excess, into the mixture of monomers (that is to say, the esterification feedstock) which has not been converted. This reduced consumption of diol thus limits the amount of diol to be recycled and thus reduces, for this reason, the energy consumption of the process.

The process also makes it possible, by replacing an acid monomer and two diol monomers with a diester monomer, to reduce the solids content of the starting polymerization monomer mixture, thus facilitating the subsequent operations, in particular the transportation of this two-phase mixture.

The following examples illustrate the invention without limiting the scope thereof.

EXAMPLES

Example 1—Comparative 5.5 t/h of terephthalic acid (PTA) are introduced into a mixing vessel equipped with a mechanical stirrer and mixed at 110° C. with 2.5 t/h of a monoethylene glycol (MEG) stream comprising 2.13 t/h of MEG originating from a storage tank and 0.37 t/h of recycled MEG originating from the section for the purification of the MEG.

The amounts of PTA and MEG introduced correspond to a PTA/MEG molar ratio of 1.23.

At 110° C., 1% by weight of PTA initially introduced is dissolved in the MEG, and the solids content by volume, defined as the ratio of the volume of solid to the total volume of the paste (solid+liquid), is 60.7% by volume. The mixture obtained forms a viscous paste.

The mixture obtained is subsequently transferred, using an appropriate pump, to a first esterification reactor operated at 260° C., 0.5 MPa, with a residence time of 1.25 h.

1.4 t/h of a vapour effluent comprising 71% by weight of water and 29% by weight of MEG are withdrawn and sent into a reflux column in order to separate the water formed by the esterification reaction and the MEG. The latter is subsequently returned to the reactor. A conversion of the PTA of 85% is obtained in the first reactor.

The liquid effluent from the first reactor is subsequently sent into a second esterification reactor operated at 260° C. and 0.2 MPa with a residence time of 1.25 h. 140 kg/h of a vapour effluent comprising 40% by weight of water and 60% by weight of MEG is withdrawn from the second reactor and sent to the reflux column. A conversion of the PTA of 92% is achieved at the outlet of the second reactor.

The liquid effluent from the second esterification reactor is sent into a third reactor operated at 275° C. and 0.033 MPa with a residence time of 0.5 h which makes it possible to drive the conversion of the PTA to 95.8% and to initiate the polycondensation. Antimony trioxide is added as polymerization catalyst at the inlet of the third reactor at a level of 220 ppm by weight. A vapour effluent comprising 70% by weight of MEG, 16.5% by weight of water, 5.5% by weight of acetaldehyde, 2.5% by weight of diethylene glycol and 5.5% by weight of oligomers is withdrawn from the third reactor and partially condensed and then sent to the section for purification of the MEG.

The liquid effluent from the third reactor is sent into a fourth reactor (polycondensation reactor) operated at 275° C. and 0.0066 MPa with a residence time of 0.5 h. A vapour effluent with the composition 60% by weight of MEG, 25% by weight of water, 6% by weight of acetaldehyde, 3% by weight of diethylene glycol and 6% by weight of oligomers is withdrawn from the fourth reactor and partially condensed and then sent to the section for purification of the MEG.

The liquid effluent from the fourth reactor is sent into a final reactor (polycondensation reactor) operated at 280° C. and 0.000013 MPa with a residence time of 1 h. A vapour effluent with the composition 57% by weight of MEG and 43% by weight of water is withdrawn and partially condensed and then sent to the section for purification of the MEG.

The section for purification of the MEG comprises a first distillation column provided with 25 plates operated at the top at 145° C. and 0.02 MPa, making it possible to separate the diethylene glycol. The bottom product from the first distillation column is sent into a second distillation column provided with 17 plates operated at the top at 100° C. and 0.1 MPa, making it possible to separate the light components, such as the water and the acetaldehyde. The MEG recovered at the end of these two distillations exhibits a purity of greater than 99.8% and is subsequently recycled to the mixing vessel.

6.25 t/h of PET are produced. The overall primary energy consumption of the production of PET is 5.8 MMkcal/h.

Example 2—According to the Invention

Production of BHET by Glycolysis of PET Flake to be Recycled 4 t/h of flakes resulting from a ground and washed PET feedstock to be recycled, consisting of 50% by weight of opaque PET and 50% by weight of coloured PET, are melted in an extruder at 250° C. and mixed with 11.4 t/h of ethylene glycol (MEG). The mixture obtained is injected into a stirred reactor, maintained at 220° C. and at a pressure of 0.4 MPa, for a residence time of 4 h. At the outlet of the reactor, the reaction effluent comprises 66% by weight of MEG, 27.4% by weight of BHET, 1.7% by weight of diethylene glycol (DEG), 0.2% by weight of water and 4.7% by weight of oligomers, pigments and other heavy compounds.

The ethylene glycol present in the reaction effluent is separated by evaporation in a sequence of five vessels at temperatures ranging from 200° C. to 124° C. and pressures from 0.1 MPa to 0.00025 MPa. At the end of this evaporation stage, an MEG stream of 10.95 t/h, composed of 97% by weight of MEG, 2.5% by weight of DEG, 0.2% by weight of water and 0.2% by weight of BHET, and a liquid stream rich in BHET of 5.17 t/h are recovered. The MEG stream is sent into first distillation provided with 25 plates and operated at the top at 0.02 MPa and 145° C., in order to separate the DEG and heavy products, then into a second distillation column provided with 17 plates and operated at the top at 100° C. and 0.1 MPa, in order to separate the water and to recover a purified MEG effluent which can subsequently be recycled to the depolymerization reactor as a mixture with a contribution of fresh MEG.

The liquid stream rich in BHET comprises 87.1% by weight of BHET, 0.2% by weight of MEG, 0.1% by weight of DEG and 12.6% by weight of oligomers, pigments and other heavy compounds.

The liquid stream rich in BHET is subsequently injected into a short path distillation at a temperature of 205° C. and a pressure of 0.00002 MPa. A prepurified liquid BHET effluent with a flow rate of 4.46 t/h is recovered by cooling the vapours in the short path distillation to 115° C. It comprises 99.8% by weight of BHET, 0.1% by weight of MEG and 0.1% by weight of DEG. A heavy residue comprising 93% by weight of oligomers, pigments and other heavy compounds and 7% by weight of BHET is also recovered at a flow rate of 0.7 t/h at the outlet of the short path distillation.

The prepurified liquid BHET stream is compressed up to 0.5 MPa and then feeds a fixed bed of active carbon having an adsorption capacity equal to 5% of its weight. At the end of this stage, a decoloured and depigmented liquid BHET stream is recovered and reinjected into a stage of preparation of a mixture of the monomers, such as that described in Example 1. The mixture prepared is subsequently subjected to the different polymerization stages, as in the process described in Example 1, for the purpose of producing PET.

The amounts of the PTA and MEG monomers and of solid BHET monomer incorporated, the solid contents in the mixture of the feedstocks obtained at 110° C., the ratio of the diol unit number to the terephthalate unit number for the production of 6.25 t/h of PET taking into account the incorporation of BHET resulting from the depolymerization process described above, for two ratios of diol units to terephthalate units (1.23 and 1.1), are given in Table 1 below. The results presented are calculated results, for different amounts of BHET introduced into the mixture, 1 mol of BHET being regarded as replacing, in the mixture, 1 mol of PTA and 2 mol of MEG, and are based on process simulations incorporating solubility data and thermodynamic data locked to experimental points.

|  |  | Example 1 | Example 2a | Example 2b | Example 2c |
|---|---|---|---|---|---|
| Amount of PET produced | [t/h] | 6.25 | 6.25 | 6.25 | 6.25 |
| Amount of PTA | [t/h] | 5.5 | 4.36 | 2.76 | 4.36 |
| Amount of MEG (fresh + recycle) | [t/h] | 2.5 | 1.65 | 0.48 | 1.39 |
| Amount of BHET incorporated | [t/h] | 0 | 1.74 | 4.2 | 1.74 |
| Diol units/terephthalate units ratio | [mol/mol] | 1.23 | 1.23 | 1.23 | 1.1 |
| Solids content | [% vol] | 60.7 | 49.2 | 31.8 | 51.5 |

It is apparent that the solids content is substantially reduced when BHET is introduced into the two-phase mixtures of monomers intended for the polymerization (esterification feedstocks) of Examples 2a, 2b and 2c, in comparison with the solids content of a two-phase mixture of monomers of Example 1: reduction in the solids content by volume of approximately 15% to approximately 48%. More particularly, at equivalent ratio of diol units to terephthalate unit, the solids content between the mixture of Example 1 and of Examples 2a and 2b changes from 60.7% by volume to respectively 49.2% by volume (fall of approximately 19%) and 31.8% by volume (fall of approximately 48%), as a function of the amount of BHET introduced into the mixture of monomers. Example 2c, in comparison with Example 2a, shows that, for one and the same amount of BHET introduced into the mixture of monomers (1.74 t/h), it is possible to prepare a two-phase monomer mixture with a reduced solids content, in comparison with a mixture not comprising BHET (51.5% by volume with respect to 60.7% by volume in Example 1), while reducing the amount of ethylene glycol contributed (only 1.39 t/h in Example 2c, in comparison with 1.65 t/h in Example 2a). Thus, the consumption of ethylene glycol starting material is reduced without this being prejudicial to the quality of the two-phase mixture, which can be easily transported to the polymerization operations.

The invention claimed is:

1. A process for producing a terephthalate polyester, comprising:
   a) a stage for preparing an esterification feedstock comprising at least one mixing section that is fed with at least one terephthalic acid feedstock and one diester monomer feedstock, wherein the amounts of at least the terephthalic acid feedstock and the diester monomer feedstock, introduced into the mixing section in the mixture, are adjusted so that the ratio of the total number of moles of diol units of formula $-[C_{(n+1)}H_{(2n+2)}O_2]-$, n being an integer greater than or equal to 1, introduced into the mixing section, with respect to the total number of moles of terephthalate units of formula $-[CO-(C_6H_4)-CO]-$ introduced into the mixing section, is between 1.0 and 2.0, wherein the mixing section is operated at a temperature of between 25° C. and 250° C. and at a pressure of greater than or equal to 0.1 MPa,
   b) a stage for esterifying the esterification feedstock resulting from stage a), in order to produce at least one reaction effluent and one aqueous effluent, wherein the esterification stage comprises at least one reaction section, operated at a temperature between 150° C. and 400° C., at a pressure between 0.05 and 1 MPa, and with a residence time between 1 and 10 h, and at least one separation section,
   c) a stage of polycondensation of the reaction effluent obtained in stage b) in order to obtain at least the terephthalate polyester and a diol effluent, the stage comprising at least one reaction section comprising at least one reactor in which the polycondensation is carried out and which is operated at a temperature between 200° C. and 400° C., at a pressure between 0.0001 and 0.1 MPa, with a residence time between 0.1 and 5 h, the reaction section also comprising at least one withdrawal of a diol effluent, and
   d) a stage for treating the diols, comprising a recovery section that is fed at least with all or part of the diol effluent resulting from stage c), in order to obtain a diol effluent to be treated, and a section for purifying the diol effluent to be treated, in order to obtain a purified diol stream.

2. A production process according to claim 1, wherein the ratio of the total number of moles of diol units of formula —[$C_{(n+1)}H_{(2n+2)}O_2$]—, introduced into the mixing section of stage a), with respect to the total number of moles of terephthalate units of formula —[CO—($C_6H_4$)—CO]—, introduced into the mixing section of stage a), is between 1.0 and 1.5.

3. A production process according to claim 1, wherein the mixing section of stage a) is additionally fed with a diol monomer feedstock which comprises a diol monomer participating in the composition of the individual unit of the terephthalate polyester.

4. A production process according to claim 1, wherein the diester monomer feedstock of stage a) comprises at least a fraction of a purified diester effluent obtained at the end of a process for the depolymerization of a polyester feedstock to be recycled.

5. A production process according to claim 4, wherein the purified diester effluent is obtained by a process for the depolymerization of a polyester feedstock to be recycled comprising at least the following stages:
  i) a depolymerization stage comprising at least one reaction section fed with the polyester feedstock to be recycled and with a glycol stream, in order to obtain a depolymerization reaction effluent,
  ii) a separation/purification stage comprising a separation section, in order to obtain a glycol effluent, and a purification section, in order to obtain a purified diester effluent, and
  iii) a stage for recycling at least a fraction of the purified diester effluent obtained in stage ii) to stage a).

6. A production process according to claim 1, wherein the diester feedstock in the mixing section of stage a) is in liquid form.

7. A production process according to claim 6, in which the preparation stage comprises a conditioning section, located upstream of the mixing section, fed at least with a diester feedstock in solid form and operated at a temperature of between 25° C. and 250° C. and at a pressure of greater than or equal to 0.1 MPa.

8. A production process according to claim 1, wherein the terephthalate polyester is polyethylene terephthalate and the diester monomer is bis(2-hydroxyethyl) terephthalate (BHET).

9. A production process according to claim 1, wherein the ratio of the total number of moles of diol units of formula-[$C_{(n+1)}H_{(2n+2)}O_2$]-, introduced into the mixing section of stage a), with respect to the total number of moles of terephthalate units of formula-[CO-($C_6H_4$)-CO]-, introduced into the mixing section of stage a), is between 1.0 and 1.3.

10. A production process according to claim 1, wherein the mixing section of stage a) is additionally fed with a diol monomer feedstock which comprises at least 70 mol % of a diol monomer participating in the composition of the individual unit of the said terephthalate polyester.

11. A production process according to claim 1, wherein the mixing section of stage a) is additionally fed with a diol monomer feedstock which comprises at least 90 mol % of a diol monomer participating in the composition of the individual unit of the said terephthalate polyester.

12. A production process according to claim 1, wherein the mixing section of stage a) is additionally fed with a diol monomer feedstock which comprises 99.5 mol % of a diol monomer participating in the composition of the individual unit of the said terephthalate polyester.

* * * * *